United States Patent [19]

Rule et al.

[11] Patent Number: 4,649,216
[45] Date of Patent: Mar. 10, 1987

[54] CARBONYLATION PROCESS FOR THE PRODUCTION OF AROMATIC ACIDS

[75] Inventors: Mark Rule; Thomas H. Larkins, Jr.; Donald W. Lane; Guy R. Steinmetz, all of Kingsport, Tenn.

[73] Assignee: Eastman Kodak Company, Rochester, N.Y.

[21] Appl. No.: 889,458

[22] Filed: Jul. 25, 1986

Related U.S. Application Data

[63] Continuation of Ser. No. 759,787, Jul. 29, 1985, abandoned.

[51] Int. Cl.$^4$ .............................................. C07C 67/36
[52] U.S. Cl. .................................................... 562/406
[58] Field of Search ......................................... 562/406

[56] References Cited

U.S. PATENT DOCUMENTS 2,565,463  8/1951  Tabet ................................... 562/406
2,914,554  11/1959 Kroeper ............................... 560/103
3,733,354  5/1973  Cassar .................................. 562/406
3,988,358  10/1976 Heck ..................................... 560/97
3,996,288  12/1976 Yukata .................................. 562/406

FOREIGN PATENT DOCUMENTS 81835  7/1959  United Kingdom .

OTHER PUBLICATIONS

Falbe, "Carbon Monoxide in Organic Synthesis," pp. 118–120 (1970).
Bauld, Tetrahedron Letters, 27, pp. 1841–1845 (1963).

Primary Examiner—Michael L. Shippen
Attorney, Agent, or Firm—Charles R. Martin; J. Frederick Thomsen

[57] ABSTRACT

This invention relates to a novel carbonylation process for the production of aromatic carboxylic acids. More particularly, this invention relates to a process for the carbonylation of aromatic iodides with carbon monoxide in the presence of a nickel catalyst in a hydrocarbon carboxylic acid reaction medium to prepare aromatic carboxylic acids.

3 Claims, No Drawings

CARBONYLATION PROCESS FOR THE PRODUCTION OF AROMATIC ACIDS

This application is a continuation of U.S. patent application Ser. No. 759,787, filed July 29, 1985, now abandoned.

DESCRIPTION

This invention relates to a novel carbonylation process for the production of aromatic carboxylic acids. More particularly, this invention relates to a process for the carbonylation of aromatic iodides with carbon monoxide in the presence of a nickel catalyst in a hydrocarbon carboxylic acid reaction medium to prepare aromatic carboxylic acids.

The preparation of carboxylic acid derivatives by carbonylation of aromatic halides catalyzed by Group VIII metal compounds is well known in the art. One such process is described in U.S. Pat. No. 2,640,071 whereby carboxylic acid derivatives are obtained from aromatic halides in a strong base reaction medium using nickel complexes as catalyst at high reaction temperatures of 250°–450° C. and a carbon monoxide pressure of 300 to 1,000 atmospheres. A typical example is the conversion of p-dichlorobenzene to dialkyl terephthalate at 345° C. and 350 atmospheres of carbon monoxide in the presence of a catalytic amount of nickel. This process requires both high temperatures and pressure. In addition, this type carbonylation requires a basic reaction medium which makes the halide by-product difficult and expensive to recover and recycle.

Another carbonylation process for preparing carboxylic acid derivatives known in the art is described in U.S. Pat. No. 3,988,358 whereby aromatic carboxylic acid esters are prepared from aromatic halides by the reaction of a starting material such as bromobenzene in a basic reaction medium with an alcohol, such as butanol, and carbon monoxide in the presence of a very expensive palladium catalyst complexed with a ligand such as a tertiary amine or phosphines, for example.

It would therefore be an advance in the state of the art to provide a more simple and less expensive process for carbonylation of aromatic halides to prepare aromatic carboxylic acids in excellent yields. It would furthermore be advantageous to provide a simple and efficient method to recover the halide by product in a useable form.

In accordance with the present invention, it has been found that aromatic iodides can be carbonylated to the desired aromatic carboxylic acids in high yields by reaction with carbon monoxide in the presence of a nickel catalyst in a carboxylic acid reaction medium. Furthermore, the reaction has high selectivity in the formation of the aromatic carboxylic acid in high purity with little or no formation of products such as aromatic carboxyl aldehydes such as 4-carboxybenzaldehyde or other such compounds even in the presence of large amounts of hydrogen.

The aromatic iodide employed as a starting material in the process of the present invention has the formula:

R(I)$_n$ wherein R represents a carbocyclic or heterocyclic aromatic group having about 5 to about 14 atoms in the ring or rings thereof and n is an integer of from 1 to about 4. Such R groups can be, for example, benzene, naphthalene, pyridine, thiophene, pyrrole, and the like.

The R groups can be substituted or unsubstituted. Such substituted R groups include as substituents halides such as chlorine and bromine, alkyl groups having up to about 12 carbon atoms, vinyl groups, carboxylic acid groups, ester groups, ether groups, and the like. Such compounds are, for example, iodobenzene, 1,3-diiodobenzene, 1,4-diiodobenzene, 2-iodonaphthalene, 2,6-diiodonaphthalene, 2,7-diiodonophthalene, methyl iodobenzoate, iodotoluene, iodobenzophenone, iodophenol, iodoanile, iododiphenyl sulfone, iodobromobenzene, 4-chloroiodobenzene, 4-bromoiodobenzene, 4-carbomethoxy iodobenzene, iodoanthracene, iodothiophene, iodobiphenyl, diiodobiphenyl, iodofuran, iodobenzoic acid, iodovinylbenzene, iodostilbene, diiodostilbene, iodobenzene sulfonic acid, iodoanisole, iododiphenylether, diiododiphenylether, iododiphenylsulfide, iodobenzaldehyde, iodopyridine, iodoanile, iodobenzene dimethylamine, 2,3,6-triiodonaphthalene, 2,3,6,8-tetraiodonaphthalene, and the like.

The aromatic iodides employed in the process of the present invention are known in the art and can be prepared by the methods known in the art. For example, T. Hudlicky et al in *The Chemistry of Halides, Pseudohalides and Azides,* Supplement D, Part 2, 1142–1158, the disclosure of which is incorporated herein by reference discloses some of such processes. One such specific process is described in J. Chem. Soc. 150 (1952) which discloses preparing iodoaromatic compounds by treatment of the aromatic compound such as benzene with iodine in the presence of silver sulfate dissolved in concentrated sulfuric acid.

In the process of this invention, the aromatic iodide is carbonylated in a carboxylic acid reaction medium, such as acetic acid, butyric acid, propionic acid, benzoic acid, and the like or mixtures thereof, with acetic acid being the most preferred. While the carbonylation reaction can tolerate substantial quantities of water, for example about 10 percent, it is preferred that the reaction be carried out under anhydrous conditions to provide good conversions. Also, the pH of the reaction medium should be less than about 5, which provides a fast and efficient carbonylation reaction.

The nickel catalyst is added to the reaction medium preferably as nickel metal or nickel salts, such as nickel acetate. The catalyst is present in a concentration of about 0.05 to 5 weight percent, preferably, about 0.1 to 1 weight percent, of the total reaction medium. The addition of an iodide salt to the carboxylic acid reaction medium is beneficial but not essential to aid in the activation of the nickel catalyst. The iodide salt can be added to the reaction medium in an amount of about 0 to 10 weight percent, preferably about 0.5 to 6 weight percent, of the total reaction medium. Under the reaction conditions the activated nickel catalyst forms one or more soluble or homogeneous species.

An iodide acceptor may also be added to the carboxylic acid reaction medium to maintain the reaction rate of the carbonylation process. However, an iodide acceptor is beneficial but not essential. Without the iodide acceptor the reaction rate decreases as the amount of iodide increases in the reaction medium. The iodide acceptor can be added in an amount of about 1 percent to about 15 weight percent, based on the amount of the carboxylic acid reaction medium, preferably about 2 to 10 weight percent. Examples of such iodide acceptors are, for example, alkali metal acetates such as lithium acetate, sodim acetate, potassium acetate and the like, preferably lithium acetate. Other iodine acceptors are, for example, alkaline earth metal acetates such as magnesium acetate, amines such as trialkylamines such as triethylamine, trimethylamine and the like and pyridine.

Alkali metal acetates can also be generated in situ by adding an alkali metal component such as lithium carbonate to the carboxylic acid reaction medium such as acetic acid to form lithium acetate. Also alkyl acetates, such as methyl acetate, can also be used as iodide acceptors. Alkyl acetates can also be generated in situ by adding an alkanol to the reaction medium which reacts with the anhydride by-product to form the alkyl acetate.

The catalytic carbonylation reaction of the present invention is conducted in the presence of carbon monoxide, which is employed in amounts such that the total reaction pressure is in the range of atmospheric pressure to about 1500 psig. Superatmospheric pressure may be employed when a volatile reactant or reaction medium is employed or when an increase in the rate of reaction is desired. Therefore, reaction pressures from 250 psig to about 1500 psig (about 1750 kPa to about 10,500 kPa) are suitable, with pressures from 500 psig up to about 1000 psig (about 3500 kPa to about 7000 kPa) being preferred, and pressures of 750 psig to about 1000 (about 5250 kPa to about 7000 kPa) being most preferred. At pressures lower than 100 psi and higher than 1000 psi a decrease is observed in the reaction rate.

The process of the present invention can be conducted at temperatures of about 125° C. to about 250° C., preferably about 175° C. to 225° C., most preferred 175° C. to 200° C. At temperatures less than 150° C. the reaction rate is slow and above 250° C., decomposition occurs with side product formation.

The aromatic iodide is added to the carboxylic acid reaction medium in an amount of about 0.1 to 50 weight percent, based on the total weight of the reaction medium. An amount less than 0.1 provides a reaction rate too slow to be economically feasible and an amount greater than 50 percent adversely affects the solubility of the reactant in the reaction medium.

The process of the present invention when conducted under anhydrous conditions allows easy recovery of the aromatic carboxylic acid and the iodide from the reaction product. The aromatic carboxylic acid can be recovered from the reaction medium by any suitable method, such as filtration. The iodide can be recovered from the reaction medium by several methods. For example, when the reaction medium is acetic acid and a stoichiometric amount of a metal acetate, such as lithium acetate, is present, acetic anhydride and lithium iodide are formed as reaction by-products. Reactive distillation of the acetic anhydride from the lithium iodide containing reaction mixture provides acetyl iodide and lithium acetate. If a metal acetate, such as lithium acetate, is not present then the acetyl iodide is formed as the reaction by-product. The acetyl iodide can be recovered by distillation. The recovered acetyl iodide can then be hydrolyzed with water to form acetic acid and hydrogen iodide which can be recovered or oxidized to recover the iodide present. Also, if methanol is present in the reaction medium, the acetyl iodide is converted into methyl iodide due to formation of the methyl acetate. The methyl iodide can be recovered from the reaction medium and its iodine values be recovered by hydrolysis.

Another method for recovery of the iodide is to add oxygen to the reaction medium which readily oxidizes the iodide to elemental iodine. The elemental iodine can be recovered by distillation, filtration or other suitable means. This method provides a good cost effective and efficient method for iodine recovery whereby the relatively expensive iodine can be recovered and recycled continuously.

Since substantially no intermediates such as aldehydes are formed during the carbonylation, the process of the present invention provides aromatic acids of very high purity. Such polycarboxylic acids, as for example, the terephthalic acid and naphthalene dicarboxylic acid are suitable for preparing polyesters without further purification as by the preparation of the diesters. This is a significant advance in the state of the art since other processes for preparing such acids as by the oxidation of xylene and 2,6-dimethyl naphthalene provide significant amounts of impurities such as the aldehydes which require removal prior to use of the polycarboxylic acids in polyester processes.

The novel process of the present invention therefore provides high purity products which are useful intermediates in the synthesis of polyesters such as polyethylene terephthalate, and other useful polymeric products.

The invention will be further illustrated by the following Examples although it will be understood that these Examples are included merely for purposes of illustration and are not intended to limit the scope of the invention.

EXAMPLE 1

Into a 330 cc autoclave was added 10 grams p-diiodobenzene, one gram nickel iodide, one gram lithium iodide, 4.5 grams lithium carbonate, seven grams acetic anhydride and 50 grams acetic acid. Carbon monoxide was fed beneath the surface of the reaction mixture at a pressure of 750 psi and the reaction mixture was heated at 200° C. for two hours. The acetic anhydride was added to the acetic acid medium to insure that the reaction medium contained substantially no water and was substantially dry. The resulting mixture was then cooled to 25° C. and filtered to remove the solid acids or carboxylic acids. The white solid product recovered was 4.5 grams which on analysis contained 91.95% by weight terephthalic acid and 0.23% by weight iodobenzoic acid. The yield of terephthalic acid based on the amount of p-diiodobenzene employed was 82.7%. No 4-carboxybenzaldehyde was detected by gas chromatographic analysis.

Similar results can be obtained using butyric, propionic acid, benzoic acid in place of acetic acid or in combination with acetic acid.

EXAMPLE 2

Into a 1 liter autoclave was added 10 grams lithium iodide, 45 grams lithium carbonate, 200 grams p-diiodobenzene, two grams nickel powder, 62 grams acetic anhydride and 440 grams acetic acid. Carbon monoxide was fed beneath the surface of the reaction mixture at 1000 psi and the reaction mixture was heated at 200° C. for four hours. The resulting mixture was then cooled to 25° C. and filtered to remove the carbonylated acid. The products recovered were 81 grams of solid product or solid carboxylic acids which analyzed as 98.94% terephthalic acid, 0.21% benzoic acid and 1.851% iodobenzoic acid. The yield of terephthalic acid based on the amount of p-diiodobenzene employed was 80%. No 4-carboxybenzaldehyde was detected by gas chromatographic analysis.

This Example shows the result obtained using nickel powder as the nickel catalyst component.

EXAMPLE 3

Example 2 was repeated except that the reaction mixture was heated for four hours at 175° C. instead of 200° C. and 750 psi carbon monoxide instead of 1000 psi. The resulting mixture was cooled to 25° C. and solid product recovered. The 98 grams of recovered material analyzed as 88.57% terephthalic acid, 0.048% benzoic acid and 7.88% iodobenzoic acid. The yield of terephthalic acid based on the amount of p-diiodobenzene employed was 86.8%. No 4-carboxybenzaldehyde was detected by gas chromatographic analysis.

This Example shows that lowering the temperature and pressure within the most preferred range did not adversely affect the reaction rate.

EXAMPLE 4

Example 3 was repeated except that 10.6 grams nickel acetate tetrahydrate was used in place of the two grams of nickel powder, 400 grams acetic acid was used in place of 440 grams acetic acid, the reaction mixture was heated at 200° C. instead of 175° C. and 1000 psi of a 95% carbon monoxide/5% hydrogen blend was used in place of 750 psi of carbon monoxide. The resulting mixture was cooled to about 25° C. and 90.5 grams of solid was recovered. The solid was analyzed and contained 96.2% terephthalic acid, 0.084% benzoic acid and 2.74% iodobenzoic acid. The yield of terephthalic acid based on the amount of p-diiodobenzene employed was 87.1%. No 4-carboxybenzaldehyde was detected by gas chromatographic analysis.

This Example shows the result obtained using nickel acetate tetrahydrate in place of nickle powder as the nickel catalyst component.

EXAMPLE 5

Into a 330 cc autoclave was added 20 grams p-diiodobenzene, 1.1 grams nickel acetate tetrahydrate, 3.0 grams lithium iodide, 4.5 grams lithium carbonate, 7 grams acetic anhydride, and 45 grams acetic acid. Carbon monoxide was fed into the reaction mixture at 1000 psi and the reaction mixture was heated at 175° C. for two hours. The resulting mixture was then cooled to 25° C. and filtered to remove the solid product. 9.4 Grams of solid was recovered, which analyzed as 0.114% benoic acid, 7.180% iodobenzoic acid, and 88.114% terephthalic acid. The yield of terephthalic acid based on the amount of p-diiodobenzene employed was 82.8%. No 4-carboxybenzaldehyde was detected by gas chromatographic analysis.

EXAMPLE 6

Into a 330 cc autoclave was added 20 grams p-diiodobenzene, 1.1 grams nickel acetate tetrahydrate, 3.0 grams lithium iodide, 40 grams acetic acid, and 10 grams methyl acetate as the iodide acceptor. The reaction mixture was heated at 175° C. for two hours and at a pressure of 1000 psi of a 95% carbon monoxide/5% hydrogen blend. About 9.7 grams of solid was obtained by filtration, which analyzed as 0.071% benzoic acid, 4.28% iodobenzoic acid, 0.015% methyl hydrogen terephthalate, and 84.95% terephthalic acid. The filtrate contained 8.45 grams acetic anhydride, 10.86 grams, methyl iodide, and 1.6 grams methyl acetate. The yield of terephthalic acid based on the amount of p-diiodobenzene employed was 82.1%. No 4-carboxybenzaldehyde was detected by gas chromatographic analysis.

This Example shows that an alkyl acetate such as methyl acetate is an effective iodide acceptor.

EXAMPLE 7

Example 6 was repeated except 10 grams of water was used in place of methyl acetate, and 100% carbon monoxide was used instead of the 95% carbon monoxide/5% hydrogen blend. About 11.3 grams of solid was recovered, which analyzed as 39.31% p-diiodobenzene, 47.63% iodobenzoic acid, and 8.95% terephthalic acid. The yield of terephthalic acid based on the amount of p-diiodobenzene employed was 10.1%. No 4-carboxybenzaldehyde was detected by gas chromatographic analysis.

This Example shows that terephthalic acid can be formed without an iodide acceptor and when water is present in an amount greater than 10 weight percent. However, the yield of terephthalic acid is substantially reduced.

EXAMPLE 8

Example 6 was repeated except that the methyl acetate was deleted and 100% carbon monoxide was used and the solvent was 20 grams acetic acid and 30 grams acetic anhydride. About 6.6 grams of solid was recovered, which analyzed at 5.02% p-diiodobenzene, 45.16% iodobenzoic acid and 36.36% terephthalic acid. The yield of terephthalic acid based on the amount of p-diiodobenzene employed was 23.9%. No 4-carboxybenzaldehyde was detected by gas chromatographic analysis.

This Example shows that without an iodide acceptor a lower terephthalic acid yield is obtained.

EXAMPLE 9

Example 5 was repeated except that a pressure of 500 psi of a 95% carbon monoxide/5% hydrogen blend was used. About 8.7 grams of solids isolated, which analyzed as 0.06% benzoic acid, 9.34% iodobenzoic acid, and 85.26% terephthalic acid. The yield of terephthalic acid based on the amount of p-diiodobenzene employed was 73.7%. No 4-carboxybenzaldehyde was detected by gas chromatographic analysis.

This Example shows that lowering the pressure to 500 psi gave a decreased reaction rate.

EXAMPLE 10

Example 1 was repeated except that 0.1 gram palladium acetate was used as the catalyst in place of the nickel powder. Only about 0.6 gram of a black solid were obtained, which analyzed as 15.5% p-diiodobenzene, 54.2% iodobenzoic acid, and 4.3% terephthalic acid. The black solid contained precipitated palladium metal. The yield of terephthalic acid was extremely low.

This Example shows that using the more expensive palladium catalyst did not provide the same result as obtained when the nickel catalyst of Example 4.

EXAMPLE 11

Example 1 was repeated using 20 grams p-diiodobenzene, 0.1 gram of palladium acetate was used in place of one gram nickel iodide, 30 grams acetic acid was used in place of 50 grams, and 15 grams 2-picoline was added. After two hours at 200° C. and 500 psi CO, about 6.4 grams of solid were isolated which analyzed 0.51% p-diodobenzene, 43.8% iodobenzoic acid and 33.96% terephthalic acid. The yield of terephthalic acid based on the amount of p-diiodobenzene employed was 28.1%.

This Example shows that the addition of a promoter to the palladium catalyst did not provide the same result as obtained with the nickel catalyst of Example 4.

EXAMPLE 12

Example 11 is repeated except that 1.1 gram of nickel acetate tetrahydrate is used in place of 0.1 gram palladium acetate, 12 ml of 2-picoline was used in place of 15 ml, and 1 ml of 48% hydrogen iodide and 10 ml acetic anhydride were added. After two hours at 200° C. and 500 psi of a 95% carbon monoxide/5% hydrogen blend about 7 grams of solid was isolated by fitration which analyzed as 91.16% terephthalic acid, 4.72% iodobenzoic acid and 0.17% benzoic acid.

This Example shows that the nickel catalyst provides a substantial difference in catalytic activity in the present carbonylation process from that obtained using the palladium catalyst.

EXAMPLE 13

Example 11 was repeated using the 95% carbon monoxide/5% hydrogen blend. About 1.9 grams of product was isolated which analyzed 26.7% p-diiodobenzene, 34.9% iodobenzoic acid, 28.1% terephthalic acid, and 0.237% 4-carboxybenzaldehyde. The yield of terephthalic acid based on the amount of p-diiodobenzene employed was 5.4%.

This Example shows that the promoted palladium catalyst not only provided low conversions but also provided a substantial amount of the 4-carboxybenzaldehyde impurity.

EXAMPLE 14

Example 4 was repeated except that only 50 grams diiodobenzene was used in place of 200 grams. The resulting mixture was cooled and 22 grams of solid was recovered. The solid was analyzed and contained 98.95% terephthalic acid and 0.75% benzoic acid. A gas chromatographic analysis showed that the solid contained substantially no 4-carboxybenzaldehyde and less than 25 ppm iodobenzoic acid.

EXAMPLE 15

Example 5 is repeated except that the amount of acetic anhydride used was increased to 10 grams and the carbon monoxide was fed at 300 psi rather than 1000 psi and at 200° C. rather than 175° C. About 8.3 grams of solid product was recovered, which analyzed as 0.18 percent benzoic acid, 0.10 percent diiodobenzene, 24.29 percent iodobenzoic acid and 58.58 percent terephthalic acid. The yield of terephthalic acid based on the diiodobenzene was 48.62%. No 4-carboxybenzaldehyde was detected by gas chromatographic analysis.

This Example shows that a lower carbon monoxide pressure gave a reduced reaction rate.

EXAMPLE 16

Into a 330 cc autoclave was added 20 grams of p-diiodobenzene, 1.1 grams nickel acetate tetrahydrate, 6.8 grams sodium iodide, 0.6 sodiium carbonate, 30 ml of acetic acid and 20 ml of acetic anhydride. A 95 percent carbon monoxide/5 percent hydrogen blend was fed to the reaction mixture at a pressure of 500 psi at 175° C. for two hours. About 8.5 grams of a solid product was recovered, which analyzed as 0.12 percent benzoic acid, 11.48 percent iodobenzoic acid and 82.32 percent ter-
ephthalic acid. The yield of terephthalic acid based on the diiodobenzene was 69.8%. No 4-carboxybenzaldehyde was detected by gas chromatographic analysis.

The Example shows that good conversions of the p-diiodobenzene to terephthalic acid are obtained using sodium iodide as the iodide salt and sodium carbonate as the iodide acceptor.

EXAMPLE 17

Into a 330 cc autoclave was added two grams diiodonaphthalene (more than 98% 2,6-diiodonaphthalene), 1.0 gram lithium carbonate, 0.4 gram lithium iodide, 1.70 grams nickel acetate tetrahydrate and 100 ml acetic acid. Carbon monoxide was fed into the reaction mixture at 1000 psi and the reaction mixture heated at 190° C. for three hours. The mixture was cooled to ambient temperature and filtered. The solid obtained was about 0.8 gram which analyzed as 0.792 gram of naphthalene dicarboxylic acid and 0.003 gram iodonaphthoic acid. The yield of naphthalene dicarboxylic acid based on the amount of diiodonaphthalene was 99.63%.

These results show that the diidoaromatic compounds can be carbonylated to the corresponding aromatic dicarboxylic acids in a carboxylic acid reaction medium using nickel catalyst in high yields under moderate reaction conditions to provide a high quality product. Also, the iodide by-product can be readily removed from the filtrate reaction medium.

The carboxylic acids prepared by the present invention are well known in the art and are useful for many purposes. For example, the dicarboxylic acids can be used in preparing thermoplastic compositions such as polyesters. Such polyesters can be formed into film, fibers and molded objects.

The invention has been described in detail with particular reference to preferred embodiments thereof, but it will be understood that variations and modification can be effected within the spirit and scope of the invention.

We claim:

1. A process for the preparation of aromatic carboxylic acids which comprises reacting an aromatic iodide having 5 to 14 atoms with carbon monoxide in the presence of a nickel catalyst in a carboxylic acid reaction medium which contains about 1 to 15 weight percent of an alkyl acetate.

2. A process for the preparation of aromatic carboxylic acids which comprises reacting an aromatic iodide having the formula

$R(I)_n$ wherein R is a phenyl or a naphthyl group and n is an integer of 1 to about 4 with carbon monoxide in the presence of a nickel catalyst in a carboxylic acid reaction medium which contains about 1 to 15 weight percent of an alkyl acetate.

3. A process for the preparation of aromatic carboxylic acids which comprises reacting an aromatic iodide having the formula

$R(I)_n$ wherein R is a phenyl or a naphthyl group and n is an integer of 1 to about 4 with carbon monoxide in the presence of a nickel catalyst in an acetic acid reaction medium which contains about 1 to 15 weight percent of methyl acetate.

* * * * *